United States Patent
Sano

(10) Patent No.: US 9,182,375 B2
(45) Date of Patent: Nov. 10, 2015

(54) MEASURING APPARATUS AND MEASURING METHOD FOR METALLIC MICROSTRUCTURES OR MATERIAL PROPERTIES

(75) Inventor: Mitsuhiko Sano, Tokyo (JP)

(73) Assignee: TOSHIBA MITSUBISHI-ELECTRIC INDUSTRIAL SYSTEMS CORPORATION, Tokyo (JP)

( * ) Notice: Subject to any disclaimer, the term of this patent is extended or adjusted under 35 U.S.C. 154(b) by 339 days.

(21) Appl. No.: 13/818,236

(22) PCT Filed: Oct. 15, 2010

(86) PCT No.: PCT/JP2010/068127
§ 371 (c)(1),
(2), (4) Date: Feb. 21, 2013

(87) PCT Pub. No.: WO2012/049764
PCT Pub. Date: Apr. 19, 2012

(65) Prior Publication Data
US 2013/0152692 A1    Jun. 20, 2013

(51) Int. Cl.
*G01N 29/00* (2006.01)
*G01N 29/24* (2006.01)
*G01N 21/17* (2006.01)

(52) U.S. Cl.
CPC ............ *G01N 29/00* (2013.01); *G01N 29/2418* (2013.01); *G01N 21/1702* (2013.01); *G01N 2291/0234* (2013.01); *G01N 2291/0289* (2013.01)

(58) Field of Classification Search
CPC .............. G01N 29/00; G01N 21/1702; G01N 2291/0234; G01N 2291/0289; G01N 29/2418
USPC .......................................................... 73/655
See application file for complete search history.

(56) References Cited

U.S. PATENT DOCUMENTS 5,526,118 A * 6/1996 Miyagawa et al. ............ 356/484
6,181,431 B1 * 1/2001 Siu ................................ 356/502
(Continued)

FOREIGN PATENT DOCUMENTS

CN      1261759 C      6/2006
CN    101473224 A      7/2009
(Continued)

OTHER PUBLICATIONS

Combined Chinese Office Action and Search Report issued Jul. 1, 2014 in Patent Application No. 201080069544.3 (with English language translation and English translation of categories of cited documents).

(Continued)

*Primary Examiner* — J M Saint Surin
(74) *Attorney, Agent, or Firm* — Oblon, Spivak, McClelland, Maier & Neustadt, L.L.P.

(57) ABSTRACT

A pulse laser oscillator (11) outputs a first laser beam, a beam splitter splitting the first laser beam into split beams, optical paths (12, 13, 14, 15, 16) propagating light of split beams split, respectively, taking different times for light propagation thereof, a condenser superimposing light of split beams propagated through the optical paths, respectively, on an identical spot of a measuring material (100), for irradiation therewith, a laser interferometer (30) irradiating the measuring material (100) with light of a second laser beam, having light intensity variations resulted from interferences between reference light and light of the second laser beam reflected or scattered, as bases to detect ultrasonic waves energized by light of the first laser beam and transmitted in the measuring material (100), a waveform analyzer (32) calculating a metallic microstructure or a material property of the measuring material (100) based on ultrasonic waves.

5 Claims, 12 Drawing Sheets

(56) References Cited

U.S. PATENT DOCUMENTS

| | | | |
|---|---|---|---|
| 6,532,821 B2* | 3/2003 | Lamouche et al. | 73/643 |
| 6,594,290 B2* | 7/2003 | Toida | 372/28 |
| 6,684,701 B2* | 2/2004 | Dubois et al. | 73/579 |
| 2006/0246693 A1* | 11/2006 | Tanaka et al. | 438/487 |
| 2007/0273952 A1* | 11/2007 | Murray | 359/238 |
| 2010/0128281 A1* | 5/2010 | Sano et al. | 356/502 |

FOREIGN PATENT DOCUMENTS

| | | |
|---|---|---|
| JP | 7-20095 A | 1/1995 |
| JP | 8 285823 | 11/1996 |
| JP | 2004 333174 | 11/2004 |
| JP | 2006 84392 | 3/2006 |
| JP | 2007 86028 | 4/2007 |
| JP | 2010-71886 A | 4/2010 |
| KR | 10-2008-0110744 | 12/2008 |
| WO | 2007 148655 | 12/2007 |

OTHER PUBLICATIONS

Office Action issued Mar. 25, 2014, in Japanese Patent Application No. 2012-538516 (with English-language translation).
Korean Office Action issued Jun. 12, 2014, in Korea Patent Application No. 10-2013-7004941 (with English translation).
International Search Report Issued Nov. 9, 2010 in PCT/JP10/68127 Filed Oct. 15, 2010.
Office Action issued Feb. 5, 2015 in Canadian Patent Application No. 2,810,630.

* cited by examiner

MEASURING APPARATUS AND MEASURING METHOD FOR METALLIC MICROSTRUCTURES OR MATERIAL PROPERTIES

TECHNICAL FIELD

Embodiments described herein generally relate to a measuring apparatus and a measuring method for metallic microstructures or material properties and those using ultrasonic waves energized by a pulse laser beam.

BACKGROUND ART

There has been a wide-spread use of ultrasonic wave for measurements of metallic microstructures or material properties. For instance, in the PTL 1 below, there is disclosed a grain size measuring apparatus for measuring grain sizes in a steel plate, using the principle that energized ultrasonic waves, transmitted through a steel plate, have different attenuation characteristics depending on grain sizes in the steel plate.

It is known that grain sizes, attenuated ultrasonic waves, and ultrasonic frequencies generally follow a scatter law to be defined (by expression 1), such that:

[Math 1]

$$D = (K^{-1} \cdot \alpha \cdot f^{-n})^{\frac{1}{n-1}} \quad \text{(expression 1)}$$

Here, denoted by a is an attenuation rate (dB/mm) of an ultrasonic wave, D is a grain size (mm), f is a frequency (MHz) of the ultrasonic wave, and n is a coefficient representing a scatter mode, typically within 1 to 4 or near.

In other words for ultrasonic waves scattered at crystal grains, the attenuation due to the scattering is promoted as the frequency becomes high. This tendency has an increased significance as the grain size increases. Accordingly, resultant differences in the attenuation rate can be based on to measure qualities of a metallic material, including the grain size, for instance.

For use to energize ultrasonic waves in a material to be measured, there are available known methods including a method employing a piezoelectric vibrator (as a first method), a method employing electromagnetic forces (as a second method), and a method employing a pulse laser beam (as a third method). Among them, the first method needs to closely attach the piezoelectric vibrator to the material to be measured, with an intervening medium (liquid) having a matched acoustic characteristic. Moreover, energized ultrasonic waves need to have frequencies typically about a few MHz or less. The second method permits ultrasonic waves to be energized in a non-contact manner, with a limited spacing (a stand-off distance) typically about a few mm from the material to be measured. Besides, this measuring material has to be a magnetic body. Namely, the second method is inapplicable to inspections such as that of a carbon steel (having a hot austenite structure) in a hot processing, that is a non-magnetic body, or of a stainless steel that also is a non-magnetic body.

In comparison with them, the third method is wide-spread because of advantages permitting non-contact measurements, large standoff distances (several 100 mm), and measurements of non-magnetic bodies.

CITATION LIST

Patent Literature

PTL 1: JP2006-84392 A

SUMMARY

Technical Problem

However, in the measurement of grain size, for instance, if energized ultrasonic waves have excessively high frequencies, the attenuation due to scattering at crystal grains develops at excessively high rates. As a result, energized ultrasonic waves become faint before reaching a detection point, where detected ultrasonic waves have worsened signal-to-noise ratios causing a debased measurement precision. On the other hand, if energized ultrasonic waves have excessively low frequencies, they undergo significant attenuation due to their diffusion irrelevant to the grain size, still constituting a difficulty in the measurement Accordingly, for measurements of metallic microstructures or material properties, energized ultrasonic waves should have frequencies selected as necessary.

In the meanwhile, according to the third method, energized ultrasonic waves have a frequency distribution typically depending on equipment-specific factors including the pulse width of a pulse laser beam in use. They are subject to the structure of a pulse laser oscillator; and hard to change. In a real sense, it was difficult to energize ultrasonic waves of adequate frequencies in accordance with an object of measurement.

For instance, there is a Q-switched solid-state pulse laser oscillator, stable in the performance and wide-spread for industrial use, which can output a pulse laser beam with a pulse width, typically in a range of several nanoseconds or more. When a material to be measured is irradiated with such a pulse laser beam, there appear ultrasonic waves energized as pulse ultrasonic waves of a half wave length, having their frequency components distributed over a range of 10 to 100 (MHz), with principal peaks within a range of 20 to 50 (MHz) or near. Detected waveforms can be processed to take out specific frequency components, using one of techniques for frequency analyses, such as a Fourier transform or a wavelet transform, as well known. However, those techniques tend to have a lower frequency resolution, as a shorter time is taken for recording phenomena being the targets to be analyzed. Pulse ultrasonic waves of the half wave length are recorded within a very short time, and provide lowered frequency resolutions. Therefore, it was difficult to avoid mixing frequency components else.

Moreover, in particular for high frequency components, their amplitudes as intensities are small, so they provide low signal-to-noise ratios. For such reasons, resultant precision was occasionally insufficient for measurements of metallic microstructures or material properties, in particular for measurements of grain sizes in a metallic material, as an issue.

Further, in order for pulse laser beams to be output with a pulse width of 1 nanosecond or less, there is a short pulse laser oscillator available in the market, which however is adapted to output a pulse laser beam with a very small light energy per pulse. In a use of a pulse laser beam from the short pulse laser oscillator, energized ultrasonic waves were faint, failing to provide detection signals with sufficient intensities, giving debased signal-to-noise ratios. Resultant precision was occasionally insufficient for measurements of metallic microstructures or material properties, in particular for measurements of grain sizes in a metallic material, as an issue.

Embodiments herein have been devised in view of the problem described. It is an object of embodiments herein to provide a measuring apparatus and a measuring method for metallic microstructures or material properties. They are to be adapted for use of a pulse laser oscillator having a typical pulse width, to energize ultrasonic vibrations sustainable over durations of one and half wavelengths or more, involving desirable frequency components more than ever. This adaptation allows for measurements of metallic microstructures or material properties, in particular for more highly precise measurements to be made of grain sizes in a metallic material within a grain size range of several micrometers or less.

Solution to Problem

To achieve the object, according to embodiments herein, there is provided a measuring apparatus for metallic microstructures or material properties including in a first aspect thereof a pulse laser oscillator, a beam splitter, optical paths, a condenser, a laser interferometer, and a waveform analyzer. The pulse laser oscillator is made up to output a first laser beam. The beam splitter is made up to split the output first laser beam into split beams. The optical paths are made up to propagate light of split beams split by the beam splitter, respectively, taking different times for light propagation thereof. The condenser is made up to superimpose light of split beams propagated through the optical paths, respectively, on an identical spot of a measuring material, for irradiation therewith. The laser interferometer is made up to irradiate the measuring material with light of a second laser beam, and have light intensity variations resulted from interferences between reference light and light of the second laser beam reflected or scattered from the measuring material, as bases to detect ultrasonic waves energized by light of the first laser beam and transmitted in the measuring material. The waveform analyzer is made up to calculate a metallic microstructure or a material property of the measuring material based on ultrasonic waves detected by the laser interferometer.

According to embodiments herein, the measuring apparatus for metallic microstructures or material properties further includes in a second aspect thereof an optical path length changer made up to change a difference in optical path length at one or more of the optical paths in the first aspect According to embodiments herein, the measuring apparatus for metallic microstructures or material properties includes in a third aspect thereof a high refractive index material provided on an optical path at one or more of the optical paths in the first aspect According to embodiments herein, the measuring apparatus for metallic microstructures or material properties has a fourth aspect, wherein among the optical paths in the first aspect, a first optical path and a second optical path requiring a longer light propagation time than that have a length difference in between, different from a length difference between the second optical path and a third optical path requiring a longer light propagation time than this.

According to embodiments herein, there is provided a measuring method for material properties including in a first aspect thereof splitting a first laser beam into split beams, propagating light of the split beams through optical paths having different light propagation times, respectively, irradiating an identical spot of a measuring material with light of split beams propagated through the optical paths, respectively, irradiating the measuring material with light of a second laser beam, having light intensity variations resulted from interferences between reference light and light of the second laser beam reflected or scattered from the measuring material, as bases to detect ultrasonic waves energized by light of the first laser beam and transmitted in the measuring material, and analyzing detected waveforms of the ultrasonic waves, calculating a metallic microstructure or a material property of the measuring material.

Advantageous Effects

As will be seen from the foregoing, according to embodiments herein, there is an adaptation achieved for use of a pulse laser oscillator having a typical pulse width, to energize ultrasonic vibrations sustainable over durations of one and half wavelengths or more, involving desirable frequency components more than ever, thereby allowing for measurements of metallic microstructures or material properties, in particular for more highly precise measurements to be made of grain sizes in a metallic material within a grain size range of several micrometers or less.

DESCRIPTION OF EMBODIMENTS

There will be described examples of embodiments herein, with reference to the drawings.

EXAMPLE 1

Description is now made of a measuring apparatus for metallic microstructures or material properties taken as an example for energizing ultrasonic waves to measure grain sizes in a metallic material, according to an example 1 of embodiments herein.

<<Configuration of the Measuring Apparatus for Metallic Microstructures or Material Properties>>

Figure 1:
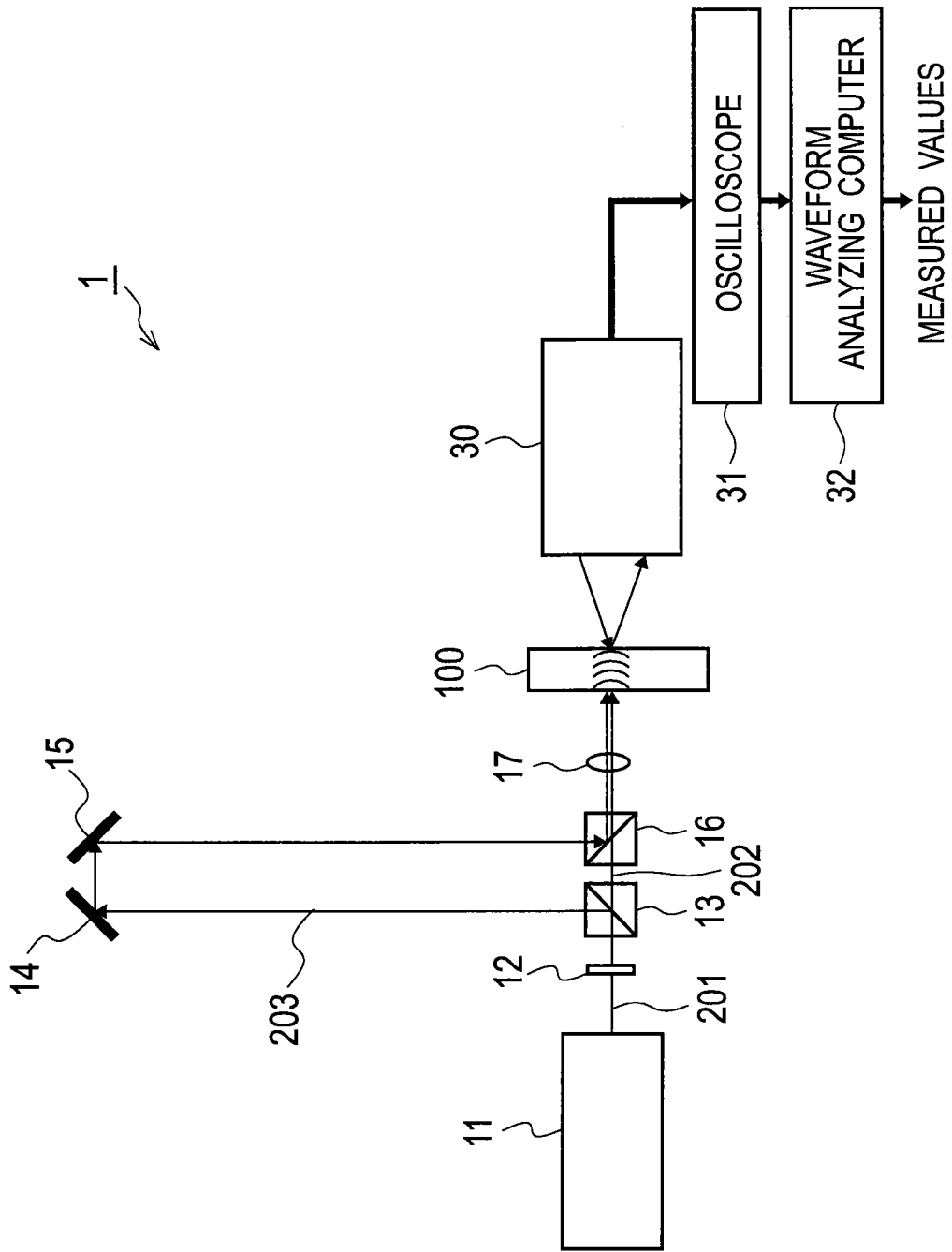
FIG. 1 is a diagram showing a configuration of a measuring apparatus for metallic microstructures or material properties according to an example 1 of embodiments herein.

FIG. 1 shows in a diagram a configuration of the measuring apparatus for metallic microstructures or material properties according to the example 1 of embodiments.

As shown in FIG. 1, the measuring apparatus 1 for metallic microstructures or material properties according to the example 1 of embodiments includes a pulse laser oscillator 11, a half wave plate 12, a first polarizing beam splitter 13, a combination of reflecting mirrors 14 and 15, a second polarizing beam splitter 16, a condensing lens 17, a laser interferometer 30, an oscilloscope 31, and a waveform analyzing computer 32.

The pulse laser oscillator 11 is provided with a Q-switched solid-state pulse laser light source employing an Nd:YAG (neodymium-doped yttrium-aluminum-garnet), and adapted to output a pulse laser beam 201 with a pulse width within degrees ranging a few nanoseconds to a dozen nanoseconds. It is noted that the pulse laser light source employed may be, for instance, a semiconductor-excited solid-state pulse laser light source, a pulse gas laser light source, a fiber laser light source, a semiconductor laser light source, or a flash lamp, or any one of those light sources combined with a laser amplifier or the like. Further, embodiments herein are applicable not simply in the case using a Q-switched solid-state pulse laser, of which output is linearly polarized, but even in cases in which the state of polarization is different as will be described later on.

The half wave plate 12 is an optical element for rotating the direction of polarization of linearly polarized light The half wave plate 12 is operable to revolve about an optical axis of the pulse laser beam 201 output from the pulse laser oscillator 11, causing the direction of polarization to be rotated by twice the revolved angle. Here, it is fixed at an angle to have a ratio of 1:1 set up between an amount of light of a first split beam 202 and an amount of light of a second split beam 203, as they are established as splits by the first polarizing beam splitter 13 to be described below The first polarizing beam splitter 13 is an optical element adapted to be permeable for a set of horizontal polarized (i.e. parallel-to-paper polarized) components of the pulse laser beam 201 to transmit as the first split beam 202, and reflective for a set of vertical polarized (i.e. normal-to-paper polarized) components of the pulse laser beam 201 to go as the second split beam 203 along an optical path oriented in a perpendicular direction relative to the above-noted optical axis.

The reflecting mirrors 14 and 15 are arranged in positions for reflecting the second split beam 203 having been reflected at the first polarizing beam splitter 13, to make it incident to the second polarizing beam splitter 16 to be described below.

The reflecting mirrors 14 and 15 are arranged to delay the time elapsed for the second split beam 203 to travel after being split to reach a measuring material 100, so that ultrasonic waves energized when the measuring material 100 is irradiated with light of the first split beam 202 overlap in part with ultrasonic waves energized when the measuring material 100 is irradiated with light of the second split beam 203. It is noted that the measuring material 100, not limited to a metallic material, may be a non-metallic material such as a glass, ceramics, or rigid plastic.

The second polarizing beam splitter 16 works to combine the first split beam 202 and the second split beam 203 with each other.

The condensing lens 17 condenses light of the first split beam 202 and the second split beam 203 combined by the second polarizing beam splitter 16, on an identical spot on the measuring material 100. This creates plasma at a surface of the measuring material 100, having ultrasonic waves energized in the measuring material 100. Then, energized ultrasonic waves travel inside the measuring material 100, reaching an opposing surface, where they appear in the form of micro vibrations. The measuring material 100 being irradiated with light of the first split beam 202 and light of the second split beam 203 thus has micro vibrations produced thereon, which can be detected in the form of electric signals by the laser interferometer 30.

The oscilloscope 31 is operable to display waveforms in accordance with electric signals detected by the laser interferometer 30.

The waveform analyzing computer 32 is adapted for operations to calculate grain sizes in the measuring material 100 based on electric signals detected by the laser interferometer 30. For instance, the waveform analyzing computer 32 is operable on waveforms detected by the laser interferometer 30, for extracting therefrom waveforms of reflection echoes in a repetition of longitudinal ultrasonic waves, followed by applying thereto a continuous wavelet transform, to determine vibration powers by frequencies. Then, the waveform analyzing computer 32 is operable on vibration powers of longitudinal echoes, for their fitting using logarithmic functions, to determine attenuation rates $\alpha$ by frequencies. These values provide a basis for use of the relationship shown (in the expression 1), to calculate grain sizes.

Figure 2:
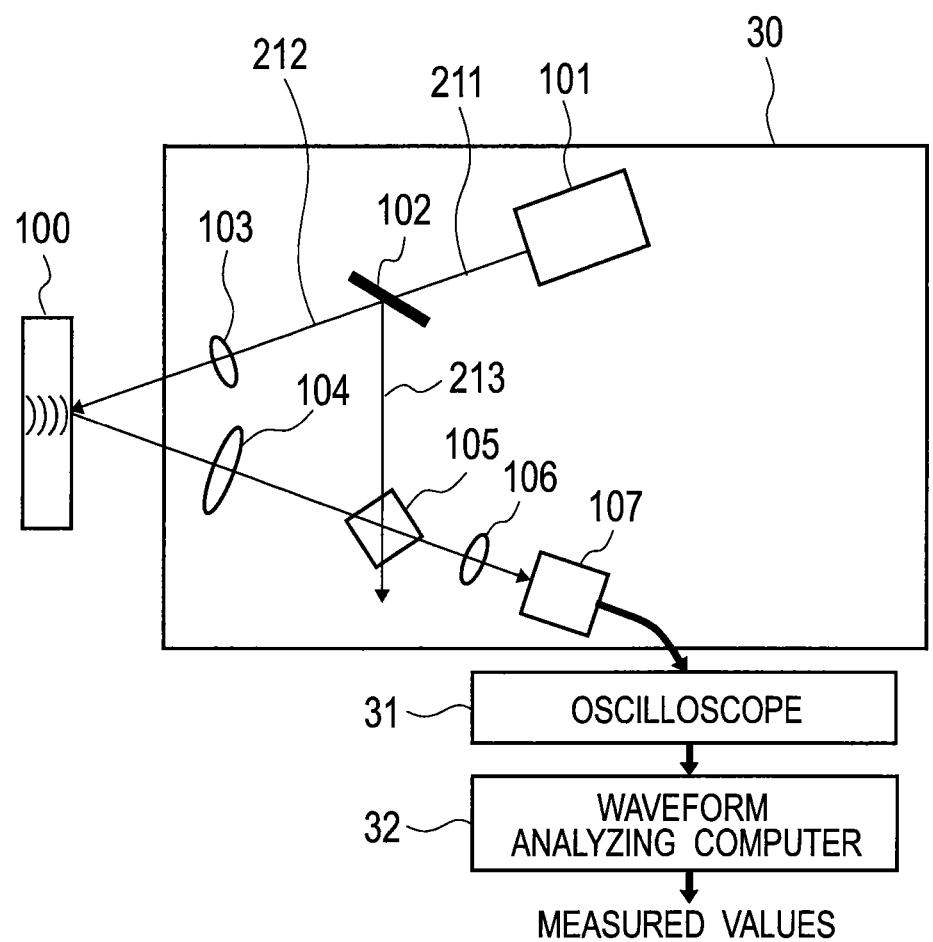
FIG. 2 is a diagram showing a configuration of a laser interferometer in the measuring apparatus for metallic microstructures or material properties according to the example 1 of embodiments.

FIG. 2 shows in a diagram a configuration of the laser interferometer 30 in the measuring apparatus 1 for metallic microstructures or material properties according to the example 1 of embodiments.

As shown in FIG. 2, the laser interferometer 30 includes a narrow line-width laser light source 101, a beam splitter 102, a combination of condensing lens 103, 104, and 106, a photorefractive crystal 105, and a photodiode 107.

The narrow line-width laser light source 101 is a light source operable to output a narrow line-width laser beam 211 with a high-wave number stability and a favorable coherency.

The beam splitter 102 works to split a laser beam 211 output from the narrow line-width laser light source 101, into two, having either transmitting as a detecting beam 211 toward the condensing lens 103, the other being refracted to go as a pump beam 213 to be incident to the photorefractive crystal 105.

The condensing lens 103 condenses light of the detecting beam 211 on a surface of the measuring material 100 opposing the surface irradiated with light of the first split beam 202 and light o the second split beam 203.

The condensing lens 104 condenses light of the detecting beam 211 reflected by the measuring material 100, to make it strike into the photorefractive crystal 105.

The photorefractive crystal 105 is made up to work when irradiated with rays of light, as a crystal responsive to their being light or dark by having charges moved in accordance therewith, inducing changes in refraction indices.

There are rays of light of the detecting beam 211 and rays of light of the pump beam 213 incoming to the photorefractive crystal 105, where they intersect each other, creating interference fringes. Then, the photorefractive crystal 105 has distributions of refraction indices produced therein in fringe shapes according to light and dark contrasts of the interference fringes. They each act as a diffractive gating, where part of light of the pump beam 213 is diffracted toward light of the detecting beam 212. In such a situation, the measuring material 100 is vibrated at a high speed. This provides the detecting beam 212 with a varied optical path, causing rays of light of the detecting beam 212 to be deviated in phases relative to distributions of refraction indices, with resultant variations in amounts of light diffracted from light of the pump beam 213 to light of the detecting beam 212.

The photodiode 107 is operable to convert fractions of light it has received into electric signals, affording to detect, as electric signals, variations in amounts of light diffracted from light of a pump beam 213 to light of a detecting beam 212 that represent a high-speed vibration on a measuring material.

<<Operations of the Measuring Apparatus for Metallic Microstructures or Material Properties>>

Description is now made of operations of the measuring apparatus 1 for metallic microstructures or material properties according to the example 1 of embodiments, with reference to FIG. 1 and FIG. 2.

The pulse laser oscillator 11 outputs a pulse laser beam 201, which is split by the first polarizing beam splitter 13 into a first split beam 202 and a second split beam 203. The first split beam 202, transmitted across the first polarizing beam splitter 13, transmits across the second polarizing beam splitter 16, too, before it arrives at a measuring material 100.

On the other hand, the second split beam 203, reflected by the first polarizing beam splitter 13, is further reflected by the reflecting mirrors 14 and 15 and still by the second polarizing beam splitter 16, before it arrives at the measuring material 100.

The first split beam 202 and the second split beam 203 thus travel different optical paths after being output from the pulse laser oscillator 11 until their arrivals at the measuring material 100, so that the second split beam 203 is delayed from the first split beam 202 to reach the measuring material 100.

Figure 3:
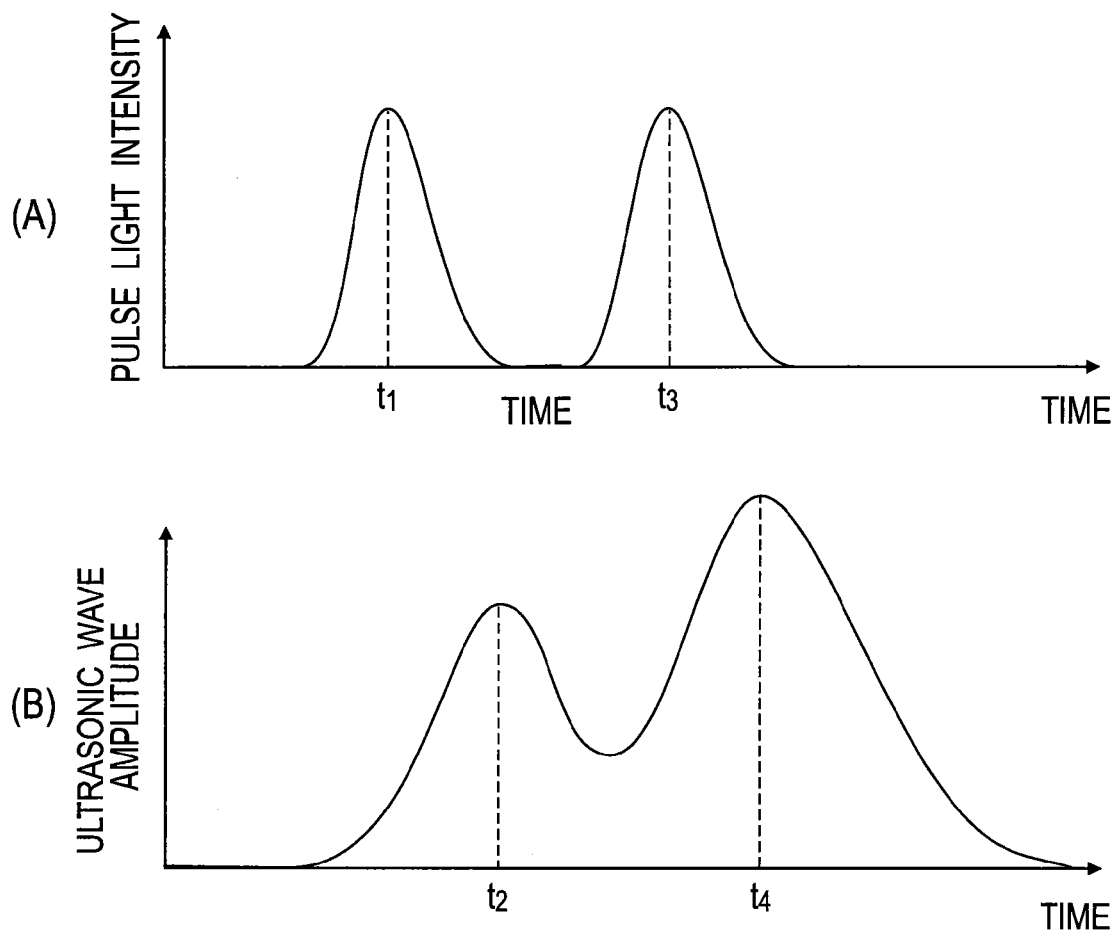
FIG. 3 includes part (A) as a graph showing an example of a sequence of pulse laser beams derived from a pulse laser oscillator in the measuring apparatus for metallic microstructures or material properties according to the example 1 of embodiments, and part (B) as a graph showing an example of a sequence of ultrasonic waves energized by the measuring apparatus for metallic microstructures or material properties according to the example 1 of embodiments.

FIG. 3(A) shows in a graph an example of a sequence of pulse laser beams derived from the pulse laser oscillator 11 in the measuring apparatus 1 for metallic microstructures or material properties according to the example 1 of embodiments. FIG. 3(B) shows in a graph an example of a sequence of ultrasonic waves energized by the measuring apparatus 1 for metallic microstructures or material properties according to the example 1 of embodiments.

FIG. 3(A) illustrates intensities of light of a first split beam 202 having reached a measuring material 100, being maximized at a point of time t1, and intensities of light of a second split beam 203 having reached the measuring material 100, being maximized at a point of time t3.

Then, FIG. 3(B) illustrates amplitudes of an ultrasonic wave energized at the point of time t1 with light of the first split beam 202 having reached the measuring material 100, being maximized at a point of time t2, and amplitudes of an ultrasonic wave energized at the point of time t3 with light of the second split beam 202 having reached the measuring material 100, being maximized at a point of time t4.

Such being the case, there is a first split beam 202 combined with a second split beam 203 delayed therefrom to reach a measuring material 100, so that ultrasonic waves energized when the measuring material 100 is irradiated with light of the first split beam 202 overlap in part with ultrasonic waves energized when the measuring material 100 is irradiated with light of the second split beam 203. Accordingly, there can be energized ultrasonic waves much involving specific frequency components.

Here, the first split beam 202 and the second split beam 203 have their arrival times at a surface of the measuring material 100, with a difference $\Delta t$ in between, which is representative (by expression 2), letting f be a frequency of energized ultrasonic waves, such that:

$$\Delta t = k/f \quad \text{(expression 2)},$$

where k is a correction factor in consideration of characteristics at rising and falling edges of a pulse laser beam, within degrees ranging 0.5 to 2.

The first split beam 202 and the second split beam 203 have their optical path lengths, with a difference $\Delta L$ in between as necessary to establish the arrival time difference $\Delta t$, which is representative (by expression 3), such that:

$$\Delta L = c_0 \cdot \Delta t \quad \text{(expression 3)},$$

where $c_0$ is the speed of light in the air, approximately $3 \times 10^8$ m/s.

Therefore, the reflecting mirrors 14 and 15 may well be arranged in position to make the optical path length difference between the first split beam 202 and the second split beam 203 equal to $\Delta L$ (i.e. in position substantially at a distance of $\Delta L/2$).

In the meanwhile, if the above-noted $\Delta t$ is excessively long relative to the pulse width of the pulse laser beam, ultrasonic waves energized with light of the first split beam 202 and ultrasonic waves energized with light of the second split beam 203 individually travel, respectively, failing to overlap, thus missing the effect of having energized ultrasonic waves much involve desirable frequency components.

Accordingly, between the times elapsed for the first split beam 202 and the second split beam 203 to arrive at a surface of the measuring material 100, the difference $\Delta t$ may well conform to a relationship to a pulse width $t_p$ of the pulse laser beam that is defined (by expression 4), such that:

$$\Delta t < a \cdot t_p \quad \text{(expression 4)},$$

where a is a constant that may well be set generally within degrees about 5 for ensured overlaps between ultrasonic waves energized with light of the first split beam 202 and ultrasonic waves energized with light of the second split beam 203.

Such being the case, given an optical path length difference $\Delta L$ calculated using (expression 2) through (expression 4), the reflecting mirrors 14 and 15 can be arranged in position to have a resultant optical path length difference equal to the $\Delta L$ (i.e. in position substantially at a distance of $\Delta L/2$), allowing for ultrasonic waves to be energized in a measuring material 100, much involving specific frequency components. As will be seen from the foregoing, according to the example 1 of embodiments, the measuring apparatus 1 for metallic microstructures or material properties employs a first split beam 202 combined with a second split beam 203 travelling an optical path requiring a longer light travel time than that, with a resultant difference between their arrival times at a surface of a measuring material 100, permitting energized ultrasonic waves to much involve specific frequency components in accordance therewith. This allows for measurements of metallic microstructures or material properties, in particular for well precise measurements to be made of grain sizes in the metallic material 100.

Moreover, according to the example 1 of embodiments, the measuring apparatus 1 for metallic microstructures or material properties includes a combination of reflecting mirrors 14 and 15 arranged to delay the time elapsed for the second split beam to travel after being split to reach the measuring material 100, so that ultrasonic waves energized when the measuring material 100 is irradiated with light of the first split beam overlap in part with ultrasonic waves energized when the measuring material 100 is irradiated with light of the second split beam. However, this configuration is not restrictive. There may well be a configuration including prisms or retroreflectors substituting for the reflecting mirrors 14 and 15.

Further, according to the example 1 of embodiments, the measuring apparatus 1 for metallic microstructures or material properties includes a laser interferometer 30 of a two-wave mixing system provided with a photorefractive crystal 105. However, this configuration is not restrictive. There may well be a configuration including, instead of the laser interferometer 30, a Fabry-Perot interferometer adapted to measure high-frequency vibrations even on a rough surface of a measuring material 100, or a Michelson interferometer adapted to measure high-frequency vibrations on a mirror-finished surface of a measuring material 100

In the example 1 of embodiments described, the measuring apparatus 1 for metallic microstructures or material properties is taken as an example adapted to measure grain sizes in a measuring material 100 that has material properties else. It is noted that this example is not restrictive. There may well be an adaptation to measure a tensile strength, yield strength, or formability of the measuring material 100, a crystalline orientation in the measuring material, or the like.

EXAMPLE 2

In the example 1 of embodiments described, the measuring apparatus 1 for metallic microstructures or material properties is taken as an example employing a pair of beam splitters to provide a difference in length between an optical path for a first split beam 202 and an optical path for a second split beam 203, whereas this example is not restrictive.

Description is now made of a measuring apparatus for metallic microstructures or material properties taken as an example employing a single beam splitter to provide a difference in length between an optical path for a first split beam 202 and an optical path for a second split beam 203, according to an example 2 of embodiments herein.

Figure 4:
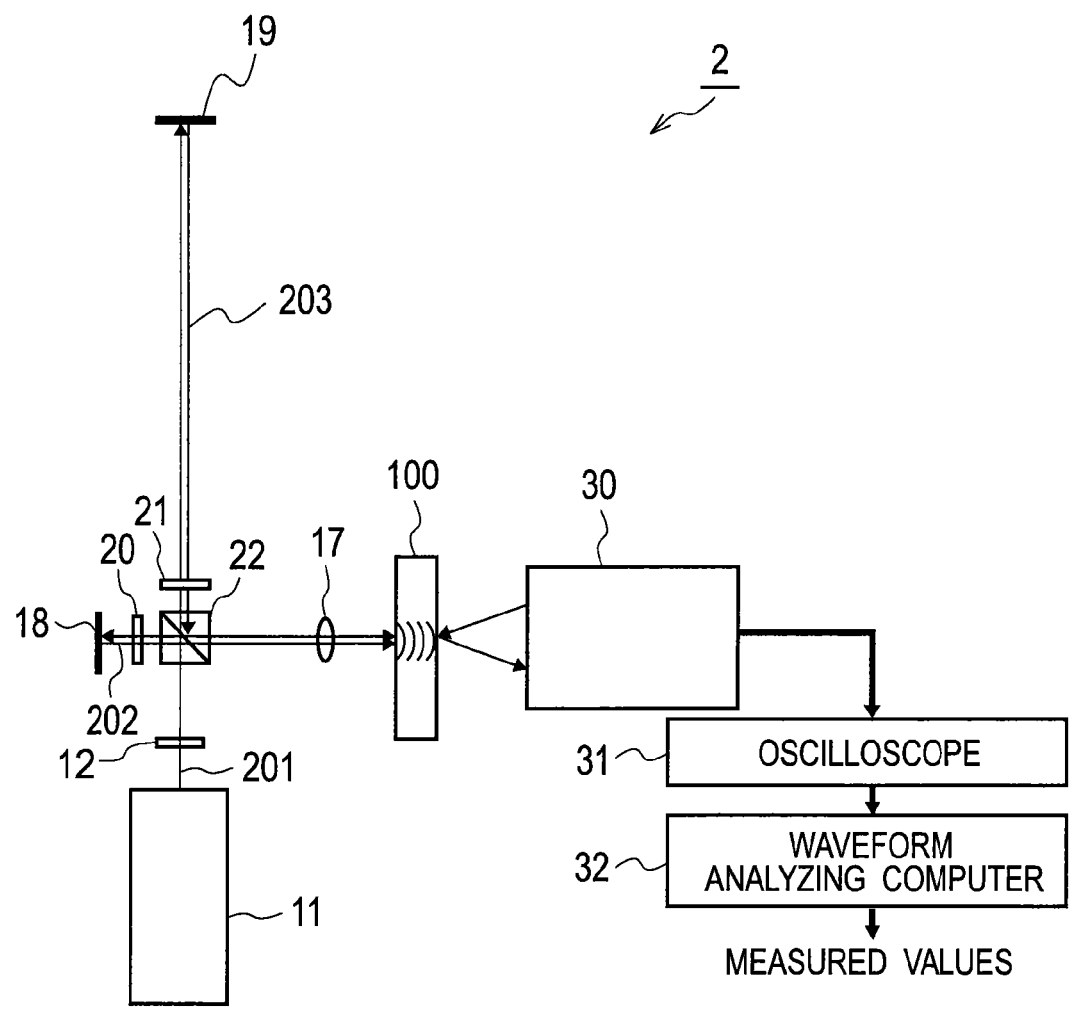
FIG. 4 is a diagram showing a configuration of a measuring apparatus for metallic microstructures or material properties according to an example 2 of embodiments herein.

FIG. 4 shows in a diagram a configuration of a measuring apparatus for metallic microstructures or material properties according to the example 2 of embodiments.

As shown in FIG. 4, the measuring apparatus 2 for metallic microstructures or material properties according to the example 2 of embodiments includes a pulse laser oscillator 11, a half wave plate 12, a polarizing beam splitter 22, a condensing lens 17, a combination of reflecting mirrors 18 and 19, a combination of quarter wave plates 20 and 21, a laser interferometer 30, an oscilloscope 31, and a waveform analyzing computer 32.

Among those constituent components, the combination of reflecting mirrors 18 and 19, the combination of quarter wave plates 20 and 21, and the polarizing beam splitter 22 will be described. For each of the other components not to be described, refer to description of a component designated by an identical reference sign, as it is identical in configuration, in the measuring apparatus 1 for metallic microstructures or material properties according to the example 1 of embodiments.

The quarter wave plate 20 is an optical element for changing a linear polarization to a circular polarization, and a circular polarization to a linear polarization. The quarter wave plate 20 has properties acting on linear polarized light, to rotate the direction of polarization by 90 degrees when the light is twice transmitted across the plate 20. The quarter wave plate 21 has a similar configuration to the quarter wave plate 20.

There is a first split beam 202 reflected by the first polarizing beam splitter 13, and circularly polarized by the quarter wave plate 20. The reflecting mirror 18 reflects this first split beam 202 toward the first polarizing beam splitter 13.

There is a second split beam 203 transmitted across the first polarizing beam splitter 13, and circularly polarized by the quarter wave plate 21. The reflecting mirror 19 reflects this second split beam 203 toward the first polarizing beam splitter 13.

The polarizing beam splitter 22 is adapted to be permeable for a set of horizontal polarized (i.e. parallel-to-paper polarized) components of a pulse laser beam 201 to transmit as a second split beam 203, and reflective for a set of vertical polarized (i.e. normal-to-paper polarized) components of the pulse laser beam 201 to go as a first split beam 202 along an optical path oriented in a perpendicular direction relative to the afore-mentioned optical axis. The polarizing beam splitter 22 is further adapted to combine a first split beam 202 reflected by the reflecting mirror 18 and a second split beam 203 reflected by the reflecting mirror 19, with each other.

Therefore, in the measuring apparatus 2 for metallic microstructures or material properties according to the example 2 of embodiments, the reflecting mirror 19 or 18 is arranged in position to make the optical path length difference between the first split beam 202 and the second split beam 203 equal to ΔL (i.e. in position substantially at a distance of ΔL/2), like the measuring apparatus 1 for metallic microstructures or material properties according to the example 1 of embodiments.

As will be seen from the foregoing, according to the example 2 of embodiments, the measuring apparatus 1 for metallic microstructures or material properties employs a single beam splitter to provide a difference between an optical path for a first split beam 202 and an optical path for a second split beam 203. The optical path difference serves to provide a difference between arrival times at a surface of a measuring material 100, which permits energized ultrasonic waves to much involve specific frequency components in accordance therewith. This allows for measurements of metallic microstructures or material properties, in particular for well precise measurements to be made of qualities of a metallic material 100, including grain sizes among others.

EXAMPLE 3

In the example 1 of embodiments described, the measuring apparatus 1 for metallic microstructures or material properties is taken as an example including a pulse laser oscillator 11 for outputting a pulse laser beam of linear polarized light, to provide a difference in length between an optical path for a first split beam 202 and an optical path for a second split beam 203, the split beams being split from the pulse laser beam of linear polarized light. It however is noted that the pulse laser beam, in no way limited to a linear polarization, may well be non-polarized.

Figure 5:
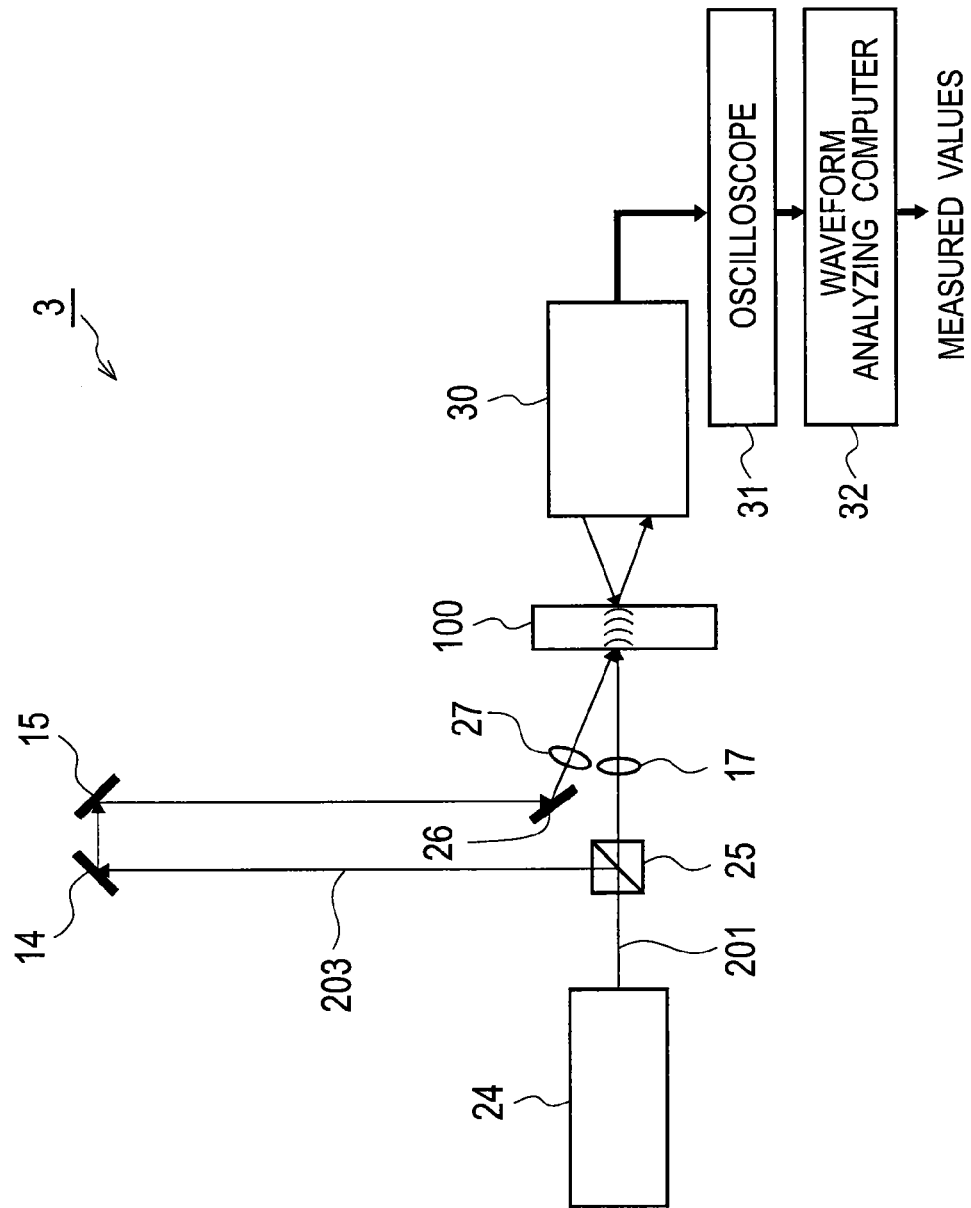
FIG. 5 is a diagram showing a configuration of a measuring apparatus for metallic microstructures or material properties according to an example 3 of embodiments herein.

FIG. 5 shows in a diagram a configuration of a measuring apparatus for metallic microstructures or material properties according to an example 3 of embodiments herein.

As shown in FIG. 5, the measuring apparatus 3 for metallic microstructures or material properties according to the example 3 of embodiments includes a pulse laser oscillator 24, a half mirror 25, a combination of condensing lens 17 and 27, a combination of reflecting mirrors 14, 15, and 26, a laser interferometer 30, an oscilloscope 31, and a waveform analyzing computer 32.

Among those constituent components, the pulse laser oscillator 24, the half mirror 25, the reflecting mirror 26, and the condensing lens 27 will be described. For each of the other components not to be described, refer to description of a component designated by an identical reference sign, as it is identical in configuration, in the measuring apparatus 1 for metallic microstructures or material properties according to the example 1 of embodiments.

The pulse laser oscillator 24 is adapted to output a pulse laser beam 201 that is a non-polarized laser beam having a pulse width within degrees ranging a few nanoseconds to a dozen nanoseconds.

The half mirror 25 is a mirror reflector for splitting the pulse laser beam 201 output from the pulse laser oscillator 24 into a first split beam 202 and a second split beam 203.

Figure 6:
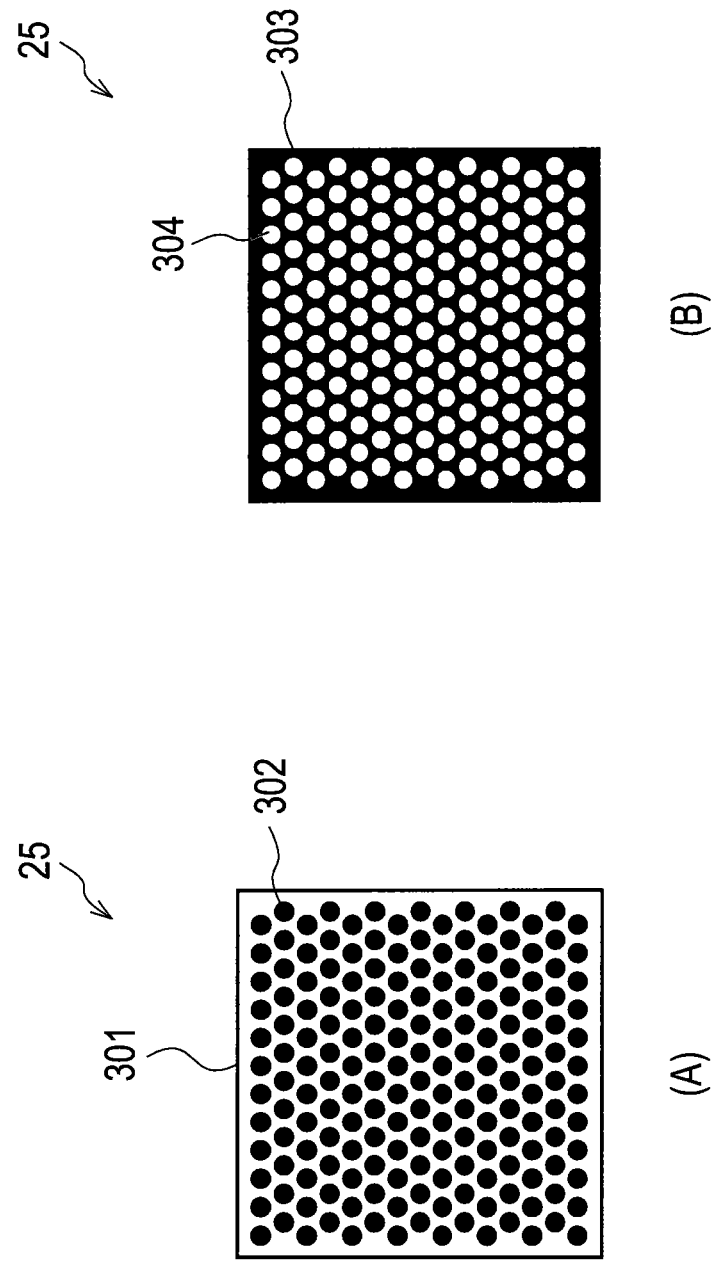
FIG. 6 gives illustrations showing examples of a half mirror 25 in the measuring apparatus 3 for metallic microstructures or material properties according to the example 3 of embodiments.

FIG. 6 shows in illustrations in part (A) and part (B) thereof examples of the half mirror 25 in the measuring apparatus 3 for metallic microstructures or material properties according to the example 3 of embodiments.

As shown in FIG. 6(A), the half mirror 25 is formed as a combination of a permeable plate 301 adapted to transmit light of a pulse laser beam 201 output from the pulse laser oscillator 24, and a set of reflective elements 302 fixed thereon. The reflective elements 302 are made to occupy a total area, whereby the permeable plate 301 has a total area retained to be 1:1 thereto.

The half mirror 25 may well have a configuration illustrated in FIG. 6(B).

FIG. 6(B) shows an example in which the half mirror 25 is provided as a combination of a reflecting mirror 303 adapted to reflect light of a pulse laser beam 201 output from the pulse laser oscillator 24, and a set of holes 304 formed therein. The holes 304 are formed to occupy a total area, whereby the reflecting mirror 303 has a total area retained to be 1:1 thereto.

There is a second split beam 203 reflected by the reflecting mirror 15. This split beam 203 is reflected by the reflecting mirror 26 toward the condensing lens 27.

A measuring material 100 is set. On a surface of the measuring material 100, there is a spot on which light of the first split beam 202 is condensed. For the second split beam 203 reflected by the reflecting mirror 26, the condensing lens 27 is arranged to condense its light on substantially the same spot as that spot, for irradiation therewith.

Therefore, in the measuring apparatus 3 for metallic microstructures or material properties according to the example 3 of embodiments, the reflecting mirrors 14, 15, and 26 are arranged as necessary to make the optical path length difference between the first split beam 202 and the second split beam 203 equal to $\Delta L$ (i.e. in a position or positions substantially at a distance of $\Delta L/2$), like the measuring apparatus 1 for metallic microstructures or material properties according to the example 1 of embodiments.

As will be seen from the foregoing, according to the example 3 of embodiments, the measuring apparatus 3 for metallic microstructures or material properties is operable, even in a situation using light of a pulse laser beam that is non-polarized for irradiating a measuring material 100, to make use of a combination of a first split beam 202 and a second split beam 203 travelling an optical path requiring a longer light travel time than that This combination serves to provide a difference between arrival times at a surface of the measuring material 100, which permits energized ultrasonic waves to much involve specific frequency components in accordance therewith. This allows for measurements of metallic microstructures or material properties, in particular for well precise measurements to be made of qualities of a metallic material 100, including grain sizes among others.

According to the example 3 of embodiments, the measuring apparatus 3 for metallic microstructures or material properties has a configuration including a half mirror 25. However, there may well be a configuration including, instead of the half mirror 25, a non-polarized beam splitter adapted to split a non-polarized laser beam.

EXAMPLE 4

In the example 1 of embodiments described, the measuring apparatus 1 for metallic microstructures or material properties is taken as an example including a laser interferometer 30 adapted to use light of a laser beam 211 for irradiating a surface of a measuring material 100 opposing a surface irradiated with light of a first split beam 202 and light of a second split beam 203. The laser interferometer 30 is further adapted to have light intensity variations resulted from interferences between reference light and light of the laser beam 211 reflected from the measuring material 100, as bases to detect ultrasonic waves energized by light of the first split beam 202 and light of the second split beam 203 and transmitted in the measuring material. It however is noted that this example is not restrictive.

Description is now made of a measuring apparatus 4 for metallic microstructures or material properties taken as an example including a laser interferometer adapted to use light of a laser beam 211 for irradiating an identical surface of a measuring material 100 irradiated with light of a first split beam 202 and light of a second split beam 203, and have light intensity variations resulted from interferences between reference light and light of the laser beam 211 reflected from the measuring material 100, as bases to detect ultrasonic waves energized by light of the first split beam 202 and light of the second split beam 203 and transmitted in the measuring material, according to an example 4 of embodiments herein.

Figure 7:
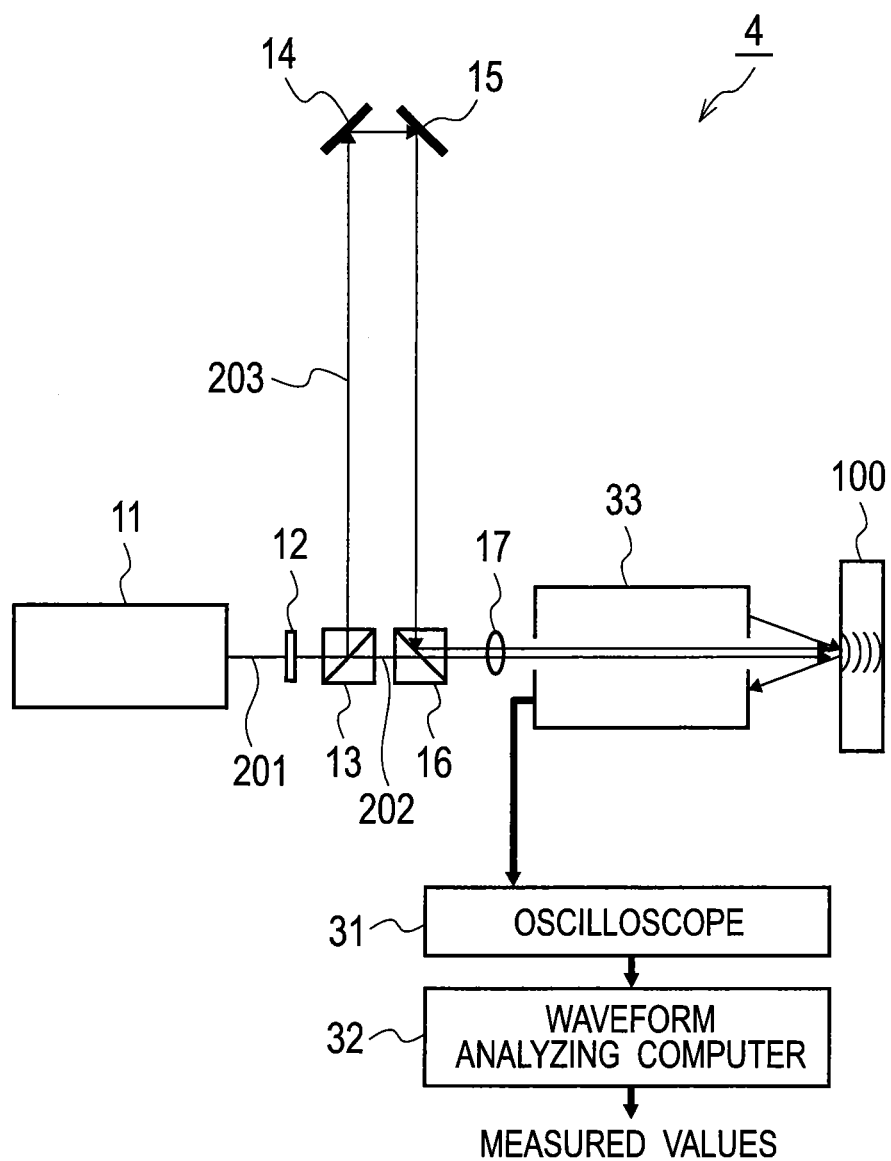
FIG. 7 is a diagram showing a configuration of a measuring apparatus for metallic microstructures or material properties according to an example 4 of embodiments herein.

FIG. 7 shows in a diagram a configuration of a measuring apparatus for metallic microstructures or material properties according to the example 4 of embodiments.

As shown in FIG. 7, the measuring apparatus 4 for metallic microstructures or material properties according to the example 4 of embodiments includes a pulse laser oscillator 11, a half wave plate 12, a first polarizing beam splitter 13, a combination of reflecting mirrors 14 and 15, a second polarizing beam splitter 16, a condensing lens 17, a laser interferometer 33, an oscilloscope 31, and a waveform analyzing computer 32.

Among those constituent components, the laser interferometer 33 will be described. For each of the other components not to be described, refer to description of a component designated by an identical reference sign, as it is identical in configuration, in the measuring apparatus 1 for metallic microstructures or material properties according to the example 1 of embodiments.

Figure 8:
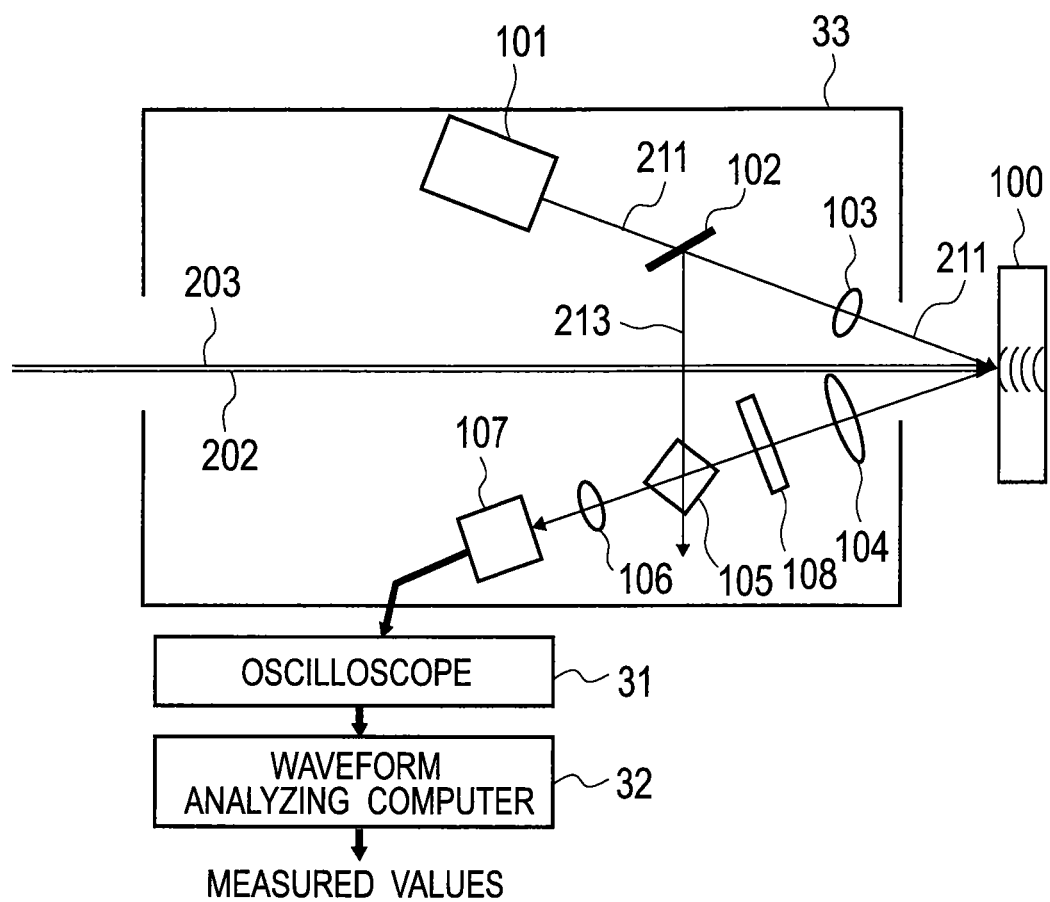
FIG. 8 is a diagram showing a configuration of a laser interferometer 33 in the measuring apparatus for metallic microstructures or material properties according to the example 4 of embodiments.

FIG. 8 shows in a diagram a configuration of the laser interferometer 33 in the measuring apparatus 4 for metallic microstructures or material properties according to the example 4 of embodiments.

As shown in FIG. 8, the laser interferometer 33 includes a narrow line-width laser light source 101, a beam splitter 102, a combination of condensing lens 103, 104, and 106, a photorefractive crystal 105, a photodiode 107, and a wavelength selecting filter 108. Among those constituent components, the wavelength selecting filter 108 will be described. For each of the other components not to be described, refer to description of a component designated by an identical reference sign, as it is identical in configuration, in the measuring apparatus 1 for metallic microstructures or material properties according to the example 1 of embodiments.

As shown in FIG. 8, the laser interferometer 33 is made up to use light of a detecting beam 211 split from a laser beam 211 to irradiate a surface of a measuring material 100 irradiated with light of a first split beam 202 and light of a second split beam 203, and condense light of the detecting beam 211 reflected on the surface of the measuring material 100, to provide as incident light to the photorefractive crystal 105.

In this situation, the wavelength selecting filter 108, installed on an optical path of light of the detecting beam 211, works to keep light of the first split beam 202 and the second split beam 203 reflected on the surface of the measuring material 100, from striking into the photorefractive crystal 105.

As will be seen from the foregoing, according to the example 4 of embodiments, the measuring apparatus 4 for metallic microstructures or material properties is operable to use light of a laser beam 211 to irradiate a surface of a measuring material 100 irradiated with light of a first split beam 202 and light of a second split beam 203, thereby having light intensity variations resulted from interferences between reference light and light of the laser beam 211 reflected from the measuring material 100, as bases to detect ultrasonic waves energized by light of the first split beam 202 and light of the second split beam 203 and transmitted in the measuring material 100.

EXAMPLE 5

In the example 1 of embodiments described, the measuring apparatus 1 for metallic microstructures or material properties is taken as an example including a combination of reflecting mirrors 14 and 15 fixed in position so that ultrasonic waves energized with light of a first split beam 202 and ultrasonic waves energized with light of a second split beam 203 overlap with each other. However, there may well be employed a combination of reflecting mirrors 14 and 15 arranged to be movable.

Description is now made of a measuring apparatus 1 for metallic microstructures or material properties taken as an example including a combination of reflecting mirrors 14 and 15 arranged to be movable so that ultrasonic waves energized with light of a first split beam 202 and ultrasonic waves energized with light of a second split beam 203 overlap with each other, according to an example 5 of embodiments herein.

Figure 9:
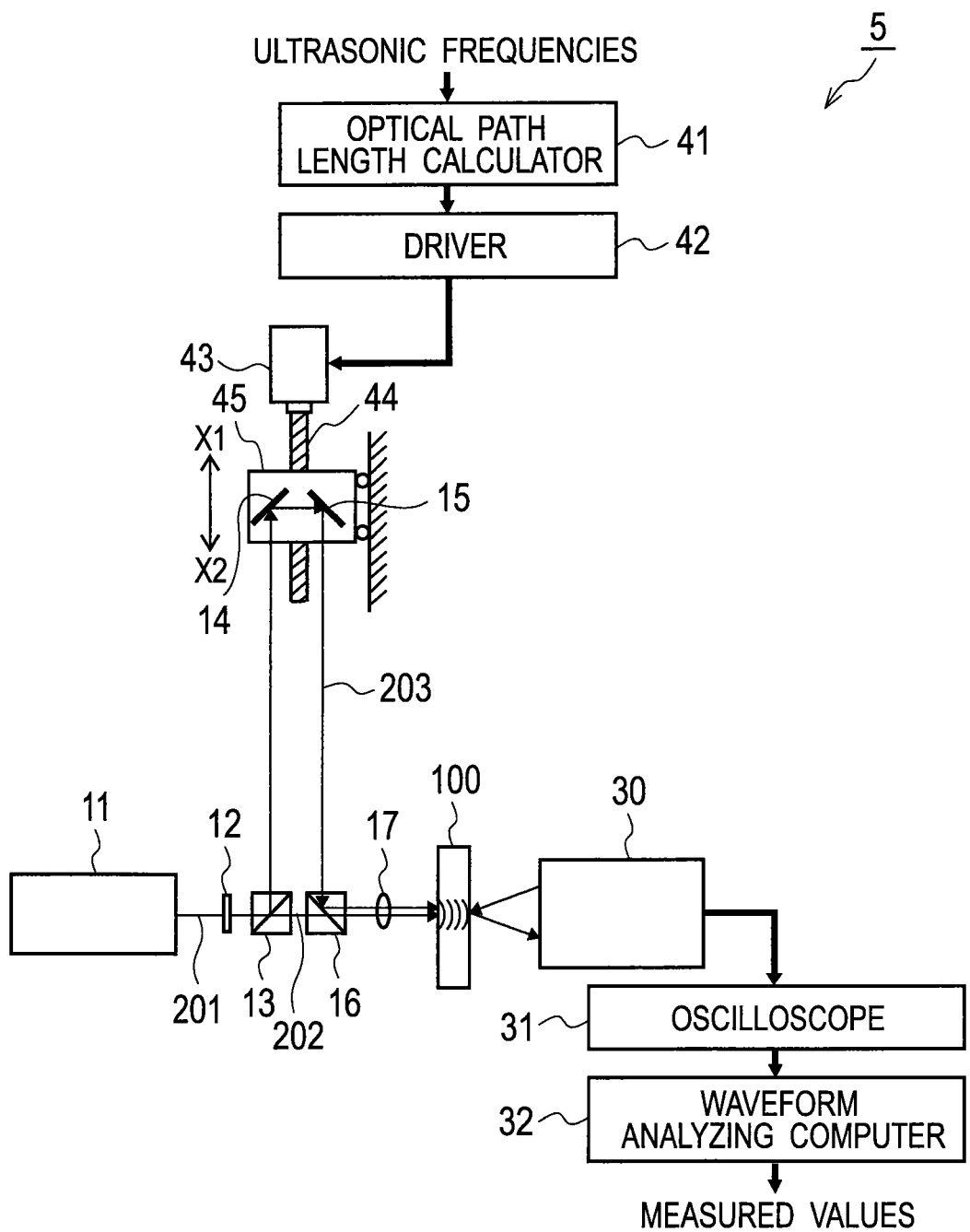
FIG. 9 is a diagram showing a configuration of a measuring apparatus for metallic microstructures or material properties according to an example 5 of embodiments herein.

FIG. 9 shows in a diagram a configuration of a measuring apparatus for metallic microstructures or material properties according to the example 5 of embodiments.

As shown in FIG. 9, the measuring apparatus 5 for metallic microstructures or material properties according to the example 5 of embodiments includes a pulse laser oscillator 11, a half wave plate 12, a first polarizing beam splitter 13, a combination of reflecting mirrors 14 and 15, a second polarizing beam splitter 16, a condensing lens 17, a laser interferometer 33, an oscilloscope 31, and a waveform analyzing computer 32. It further includes an optical path length calculator 41, a driver 42, a motor 43, a revolving shaft 44, and a mirror cabinet 45.

Among those constituent components, the optical path length calculator 41, the driver 42, the motor 43, the revolving shaft 44, and the mirror cabinet 45 will be described. For each of the other components not to be described, refer to description of a component designated by an identical reference sign, as it is identical in configuration, in the measuring apparatus 1 for metallic microstructures or material properties according to the example 1 of embodiments. Here, the optical path length calculator 41, the driver 42, the motor 43, the revolving shaft 44, and the mirror cabinet 45 constitute a section, which is referred to as an optical path length changer.

The optical path length calculator 41 serves when a frequency of an ultrasonic wave to be energized is input in accordance with the user's operation, to calculate an optical path length for a second split beam 203, as necessary, to energize ultrasonic waves of the input frequency.

The driver 42 is adapted to generate a drive signal to establish the optical path length for the second split beam 203, as it is calculated by the optical path length calculator 41.

The motor 43 follows the drive signal generated by the driver 42 to make the revolving shaft 44 revolve, thereby causing the mirror cabinet 45 to move in either direction X1 or X2, carrying the combination of reflecting mirrors 14 and 15 accommodated therein.

As will be seen from the foregoing, according to the example 5 of embodiments, the measuring apparatus 5 for metallic microstructures or material properties is operable to make use of a combination of a first split beam 202 and a second split beam 203 travelling an optical path requiring a longer light travel time than that, in the manner of rendering variable the difference between arrival times at a surface of a measuring material 100. This permits energized ultrasonic waves to much involve specific frequency components, as necessary, along with the context of measurement, thus affording to change ultrasonic frequency components available for the measurement, in an adequate manner complying with the context of measurement. This allows for measurements of metallic microstructures or material properties, in particular for well precise measurements to be made of grain sizes in the metallic material 100.

According to the example 5 of embodiments, the measuring apparatus 5 for metallic microstructures or material properties employs a motor to be driven to displace a mirror cabinet 45 in either direction X1 or X2. However, this is not restrictive. There may well be use of a hydraulic or pneumatic cylinder to move a mirror cabinet 45 in either direction X1 or X2.

EXAMPLE 6

In the example 1 of embodiments described, the measuring apparatus 1 for metallic microstructures or material properties is taken as an example including a combination of reflecting mirrors 14 and 15 arranged in position so that ultrasonic waves energized with light of a first split beam 202 and ultrasonic waves energized with light of a second split beam 203 overlap with each other. However, there may well be a high refractive index material installed in an optical path of a second split beam, to make the second split beam travel a shorter optical path to arrive at a measuring material 100.

Description is now made of a measuring apparatus for metallic microstructures or material properties taken as an example including a high refractive index material installed along an optical path of a second split beam, according to an example 6 of embodiments herein.

Figure 10:
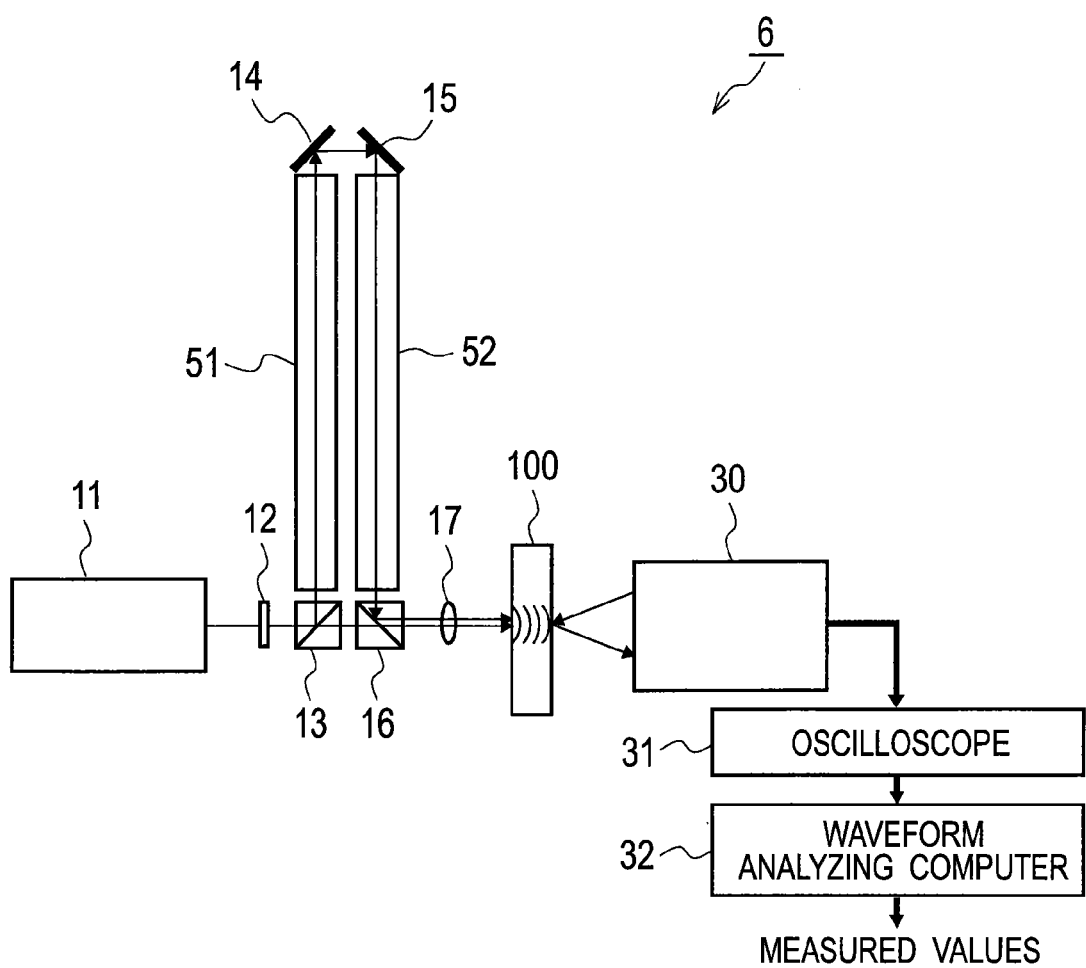
FIG. 10 is a diagram showing a configuration of a measuring apparatus for metallic microstructures or material properties according to an example 6 of embodiments herein.

FIG. 10 shows in a diagram a configuration of a measuring apparatus for metallic microstructures or material properties according to the example 6 of embodiments.

As shown in FIG. 10, the measuring apparatus 6 for metallic microstructures or material properties according to the example 6 of embodiments includes a pulse laser oscillator 11, a half wave plate 12, a first polarizing beam splitter 13, a combination of reflecting mirrors 14 and 15, a second polarizing beam splitter 16, a condensing lens 17, a laser interferometer 30, an oscilloscope 31, a waveform analyzing computer 32, and a combination of high refractive index materials 51 and 52.

Among those constituent components, the combination of high refractive index materials 51 and 52 will be described. For each of the other components not to be described, refer to description of a component designated by an identical reference sign, as it is identical in configuration, in the measuring apparatus 1 for metallic microstructures or material properties according to the example 1 of embodiments.

The high refractive index material 51 is installed along a course of an optical path of a second split beam 203 extending between the first polarizing beam splitter 13 and the reflecting mirror 14. The high refractive index material 52 is installed along a course of the optical path of the second split beam 203 extending between the reflecting mirror 15 and the second polarizing beam splitter 16.

The high refractive index materials 51 and 52 are each formed by using a medium that has a higher refractive index than the air, so that the optical path of the second split beam 203 has a contracted length.

In the meanwhile, in the high refractive index materials 51 and 52, that is, in the medium having a higher refractive index than the air, light has a slower speed $c_1$ than in the air, which is representative (by expression 5), such that:

$$c_1 = c_0/n \quad \text{(expression 5)},$$

where n is a refractive index of the high refractive index materials 51 and 52. Therefore, according to the example 6 of embodiments, the measuring apparatus 6 for metallic microstructures or material properties has a length difference $\Delta L'$ between an optical path of a first split beam 202 and the optical path of the second split beam 203 which is representative (by expression 6), such that:

$$\Delta L' = c_1 \cdot \Delta t = c_0 \cdot t/n \quad \text{(expression 6)}.$$

Accordingly, the optical path of the second split beam 203 can be cut down in length, for instance, by approximately 31% when the high refractive index materials 51 and 52 are made of a quartz glass that has a refractive index n equal to 1.45.

It is noted that the high refractive index materials 51 and 52 each have an input end face and an output end face for the second split beam 203 to strike in and out. It is preferable to apply an AR (anti-reflective) coat to each end, to suppress losses in light amount due to reflection at the end faces.

As will be seen from the foregoing, according to the example 6 of embodiments, the measuring apparatus 6 for metallic microstructures or material properties includes a high refractive index material set installed on an optical path of a second split beam 203. Accordingly, even in a situation suffering from constraints, such as those due to an installation space of equipment, in which the optical path of the second split beam 203 might otherwise have failed to save a sufficient length as the high refractive index material set is unused, it is still possible for the measuring apparatus 6 to employ a first split beam 202 combined with the second split beam 203 travelling the optical path requiring a longer light travel time than that, with a resultant difference between their arrival times at a surface of a measuring material 100, permitting energized ultrasonic waves to much involve specific frequency components in accordance therewith. This allows for measurements of metallic microstructures or material properties, in particular for well precise measurements to be made of grain sizes in a metallic material.

EXAMPLE 7

In the example 3 of embodiments described, the measuring apparatus 1 for metallic microstructures or material properties is taken as an example including a pulse laser oscillator 24 adapted to output a pulse laser beam as a non-polarized laser beam, and having a first split beam 202 and a second split beam 203 split from the pulse laser beam, providing a length difference between their optical paths.

Description is now made of a measuring apparatus 1 for metallic microstructures or material properties taken as an example including a pulse laser oscillator 24 adapted to output a pulse laser beam as a non-polarized laser beam, and having a first split beam 202, a second split beam 203, and a third split beam split from the pulse laser beam, providing length differences among their optical paths, according to an example 7 of embodiments herein.

Figure 11:
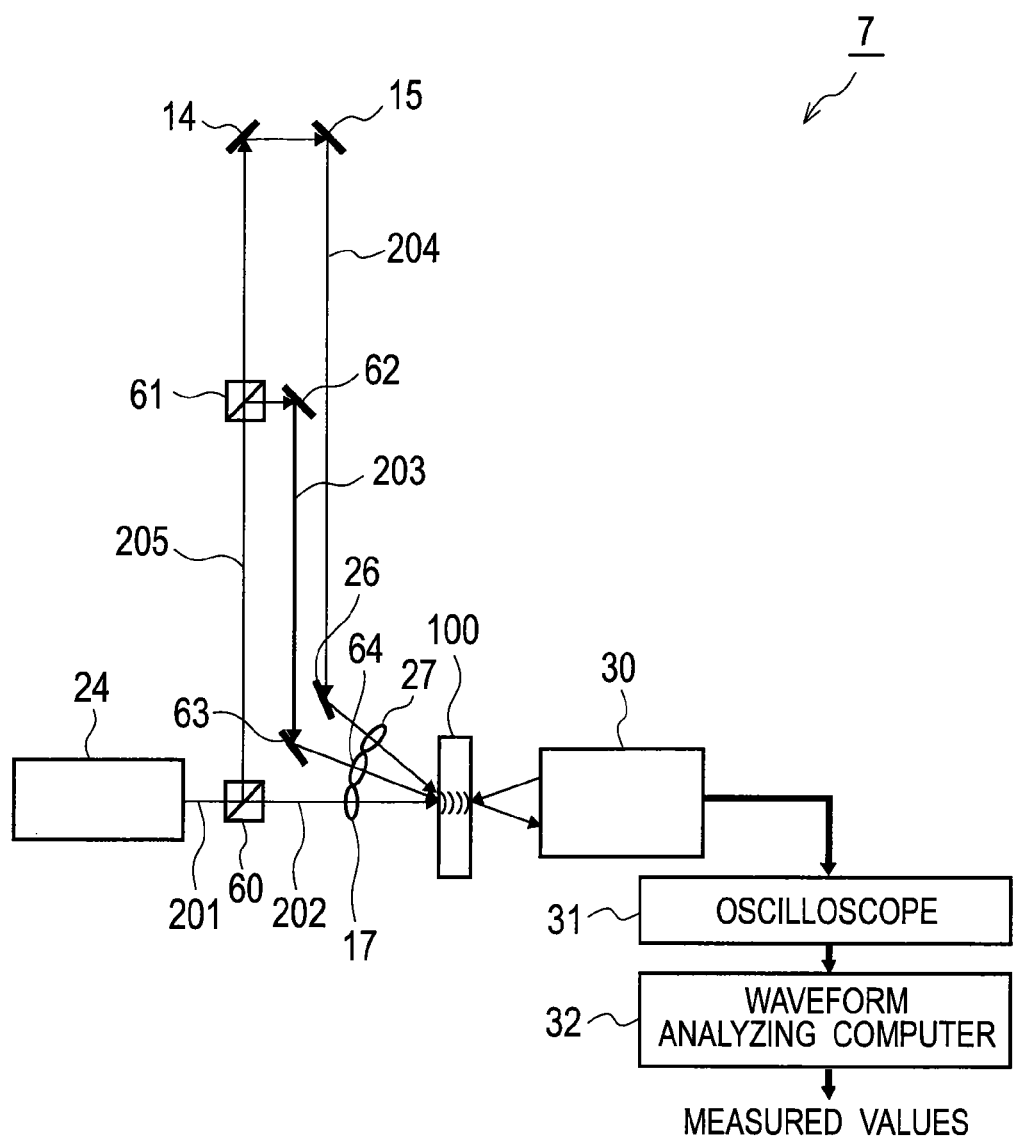
FIG. 11 is a diagram showing a configuration of a measuring apparatus for metallic microstructures or material properties according to an example 7 of embodiments herein.

FIG. 11 shows in a diagram a configuration of a measuring apparatus for metallic microstructures or material properties according to the example 7 of embodiments.

As shown in FIG. 11, the measuring apparatus 7 for metallic microstructures or material properties according to the example 7 of embodiments includes a pulse laser oscillator 24, a combination of condensing lens 17, 27, and 64, a combination of reflecting mirrors 14, 15, 26, 62, and 63, a combination of non-polarizing beam splitters 60 and 61, a laser interferometer 30, an oscilloscope 31, and a waveform analyzing computer 32.

Among those constituent components, the condensing lens 64, the reflecting mirrors 62 and 63, and the non-polarizing beam splitters 60 and 61 will be described. For each of the other components not to be described, refer to description of a component designated by an identical reference sign, as it is identical in configuration, in the measuring apparatus 3 for metallic microstructures or material properties according to the example 3 of embodiments.

There is a pulse laser beam 201 output from the pulse laser oscillator 24, and split at the non-polarizing beam splitter 60 into a first split beam 202 and a fourth split beam 205. The first split beam 202 is transmitted across the non-polarizing beam splitter 60. The fourth split beam 205 is reflected by the non-polarizing beam splitter 60 toward the non-polarizing beam splitter 61. The non-polarizing beam splitter 60 is made up to give the first split beam 202 an amount of light to be 1:2 in the ratio to an amount of light it gives the fourth split beam 205.

The fourth split beam 205, split at the non-polarizing beam splitter 60, enters the non-polarizing beam splitter 61, where it is split into a second split beam 203 and a third split beam 204. The second split beam 203 is reflected by the non-polarizing beam splitter 61 toward the reflecting mirror 62. The third split beam 204 is transmitted across the non-polarizing beam splitter 61. Here, the non-polarizing beam splitter 61 is made up to give the second split beam 203 an amount of light to be 1:1 in the ratio to an amount of light it gives the third split beam 204.

The second split beam 203, split at the non-polarizing beam splitter 61, is reflected by the reflecting mirrors 62 and 63 toward the condensing lens 64.

A measuring material 100 is set. On a surface of the measuring material 100, there is a spot on which light of the first split beam 202 is condensed. For the second split beam 203 reflected by the reflecting mirrors 62 and 63, the condensing lens 64 is arranged to condense its light on substantially the same spot as that spot, for irradiation therewith.

The non-polarizing beam splitters 60 and 61, the reflecting mirrors 26, 62, and 63, and the condensing lens 64 are arranged in positions to establish an optical path for the second split beam 203, such that ultrasonic waves energized when the measuring material 100 is irradiated with light of the first split beam 202 overlap in part with ultrasonic waves energized when the measuring material 100 is irradiated with light of the second split beam 203.

Further, the non-polarizing beam splitters 60 and 61, the reflecting mirrors 14, 15, and 26, and the condensing lens 27 are arranged in positions to establish an optical path for the third split beam 204, such that ultrasonic waves energized when the measuring material 100 is irradiated with light of the second split beam 203 overlap in part with ultrasonic waves energized when the measuring material 100 is irradiated with light of the third split beam 204.

As will be seen from the foregoing, according to the example 7 of embodiments, the measuring apparatus 7 for metallic microstructures or material properties is operable to employ, among others derived from an output pulse laser beam, a combination of a first split beam 202 and a second split beam 203 travelling an optical path requiring a longer light travel time than that, with a resultant difference between their arrival times on a surface of a measuring material 100, and a combination of the second split beam 203 and a third split beam 204 travelling an optical path requiring a longer light travel time than that, with a resultant difference between their arrival times on the surface of the measuring material 100, in the manner of rendering the differences different from each other. This permits a single shot of pulse laser beam to energize two kinds of ultrasonic waves with different frequency components, allowing for measurements of metallic microstructures or material properties, in particular for well precise measurements to be made of grain sizes in a metallic material.

Figure 12:
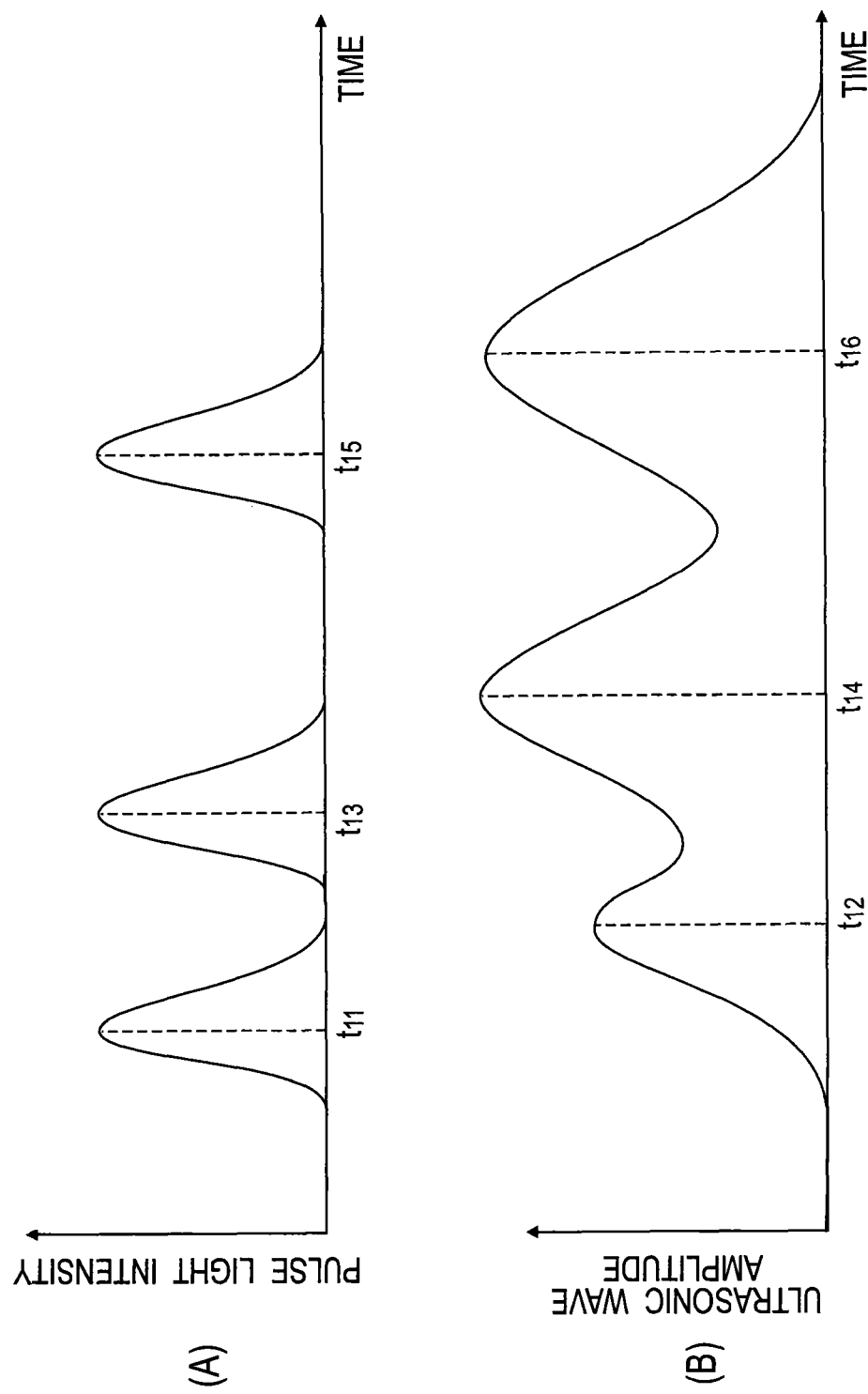
FIG. 12 includes part (A) as a graph showing an example of a sequence of pulse laser beams derived from a pulse laser oscillator in the measuring apparatus for metallic microstructures or material properties according to the example 7 of embodiments, and part (B) as a graph showing an example of a sequence of ultrasonic waves energized by the measuring apparatus 7 for metallic microstructures or material properties according to the example 7 of embodiments.

FIG. 12(A) as a graph showing an example of a sequence of pulse laser beams derived from a pulse laser oscillator in the measuring apparatus for metallic microstructures or material properties according to the example 7 of embodiments. FIG. 12(B) shows in a graph an example of a sequence of ultrasonic waves energized by the measuring apparatus 7 for metallic microstructures or material properties according to the example 7 of embodiments.

FIG. 12(A) illustrates intensities of light of a first split beam 202 having reached a measuring material 100, being maximized at a point of time t11, intensities of light of a second split beam 203 having reached the measuring material 100, being maximized at a point of time t13, and intensities of light of a third split beam 204 having reached the measuring material 100, being maximized at a point of time t15.

Then, FIG. 12(B) illustrates amplitudes of an ultrasonic wave energized at the point of time t11 with light of the first split beam 202 having reached the measuring material 100, being maximized at a point of time t12, amplitudes of an ultrasonic wave energized at the point of time t13 with light of the second split beam 203 having reached the measuring material 100, being maximized at a point of time t14, and amplitudes of an ultrasonic wave energized at the point of time t15 with light of the second split beam 204 having reached the measuring material 100, being maximized at a point of time t16.

Such being the case, there is a first split beam 202 combined with a second split beam 203 delayed therefrom to reach a measuring material 100, so that ultrasonic waves energized when the measuring material 100 is irradiated with light of the first split beam 202 overlap in part with ultrasonic waves energized when the measuring material 100 is irradiated with light of the second split beam 203.

Further, the second split beam 203 is combined with a third split beam 204 delayed therefrom to reach the measuring material 100, so that ultrasonic waves energized when the measuring material 100 is irradiated with light of the second split beam 203 overlap in part with ultrasonic waves energized when the measuring material 100 is irradiated with light of the third split beam 204.

Accordingly, a single shot of pulse laser beam can serve to energize two kinds of ultrasonic waves with different frequency components, allowing for measurements of metallic microstructures or material properties, in particular for well precise measurements to be made of grain sizes in a metallic material.

It is noted that according to the example 7 of embodiments, the measuring apparatus 7 for metallic microstructures or material properties may well have a set of high refractive index materials installed on an optical path of a second split beam 203 and an optical path of a third split beam 204, like the measuring apparatus 6 for metallic microstructures or material properties according to the example 6 of embodiments.

Industrial Applicability

Embodiments herein are applicable to quality measurements of rolling materials in hot rolling mills.

Reference Signs List 1, 2, 3, 4, 5, 6, or 7 . . . a measuring apparatus for metallic microstructures or material properties
11 or 24 . . . a pulse laser oscillator
12 . . . a half wave plate
13 . . . a first polarizing beam splitter
14, 15, 18, 19, 26, 62, or 63 . . . a reflecting mirror
16 . . . a second polarizing beam splitter
17, 27, or 64 . . . a condensing lens
20 or 21 . . . a quarter wave plate
22 . . . a polarizing beam splitter
25 . . . a half mirror
30 or 33 . . . a laser interferometer
31 . . . an oscilloscope
32 . . . a waveform analyzing computer
41 . . . an optical path length calculator
42 . . . a driver
43 . . . a motor
44 . . . a revolving shaft
45 . . . a mirror cabinet
51 or 52 . . . a high refractive index material,
60 or 61 . . . a non-polarizing beam splitter
60 . . . a non-polarizing beam splitter
100 . . . a measuring material
101 . . . a narrow line-width laser light source
102 . . . a beam splitter
103, 104, or 106 . . . a condensing lens
105 . . . a photorefractive crystal
107 . . . a photodiode
108 . . . a wavelength selecting filter

The invention claimed is:

1. A measuring apparatus for metallic microstructures or material properties, comprising:
   a pulse laser oscillator configured to output a first laser beam;
   a beam splitter configured to split the output first laser beam into split beams;
   optical paths configured to propagate light of the split beams split by the beam splitter, respectively, taking different times for light propagation thereof;
   a condenser configured to superimpose the light of the split beams propagated through the optical paths, respectively, on an identical spot of a measuring material, for irradiation therewith;
   a laser interferometer configured to irradiate the measuring material with light of a second laser beam, and have light intensity variations resulting from interferences between reference light and light of the second laser beam reflected or scattered from the measuring material, as bases to detect ultrasonic waves energized by the light of the split beams, the ultrasonic waves at least partially overlapping after being transmitted in the measuring material; and
   a waveform analyzer configured to calculate a metallic microstructure or a material property of the measuring material based on ultrasonic waves detected by the laser interferometer,
   wherein a difference between light propagation times of two of the split beams that arrive at the measuring material consecutively is $\Delta t$, a pulse width of the first laser beam is tp, a constant representing overlap between said ultrasonic waves energized by said two of the split beams that arrive at the measuring material consecutively is a, and a relation $\Delta t < a \cdot tp$ is satisfied.

2. The measuring apparatus for metallic microstructures or material properties according to claim 1, wherein,
   further comprising an optical path length changer configured to change a difference in optical path length at one or more of the optical paths.

3. The measuring apparatus for metallic microstructures or material properties according to claim 1, wherein,
   comprising a high refractive index material provided on an optical path at one or more of the optical paths.

4. The measuring apparatus for metallic microstructures or material properties according to claim 1, wherein among the optical paths, a length difference between a first optical path requiring a first light propagation time and a second optical path requiring a second light propagation time longer than the first light propagation time is different from a length difference between the second optical path and a third optical path requiring a third light propagation time longer than the second light propagation time.

5. A measuring method for metallic microstructures or material properties, comprising:
   splitting a first laser beam into split beams;
   propagating light of the split beams through optical paths having different light propagation times, respectively;
   irradiating an identical spot of a measuring material with the light of the split beams propagated through the optical paths, respectively;
   irradiating the measuring material with light of a second laser beam;
   having light intensity variations resulting from interferences between reference light and light of the second laser beam reflected or scattered from the measuring material, as bases to detect ultrasonic waves energized by the light of the split beams, the ultrasonic waves at least partially overlapping after being transmitted in the measuring material; and
   analyzing detected waveforms of the ultrasonic waves, calculating a metallic microstructure or a material property of the measuring material,
   wherein a difference between light propagation times of two of the split beams that arrive at the measuring material consecutively is $\Delta t$, a pulse width of the first laser beam is tp, a constant representing overlap between said ultrasonic waves energized by said two of the split beams that arrive at the measuring material consecutively is a, and a relation $\Delta t < a \cdot tp$ is satisfied.

* * * * *